(12) United States Patent
Siess

(10) Patent No.: US 9,872,948 B2
(45) Date of Patent: Jan. 23, 2018

(54) INTRACARDIAC PUMPING DEVICE

(75) Inventor: Thorsten Siess, Wuerselen (DE)

(73) Assignee: ABIOMED EUROPE GMBH, Aachen (DE)

( * ) Notice: Subject to any disclaimer, the term of this patent is extended or adjusted under 35 U.S.C. 154(b) by 3076 days.

(21) Appl. No.: 10/566,423

(22) PCT Filed: Jul. 24, 2004

(86) PCT No.: PCT/EP2004/008321
§ 371 (c)(1),
(2), (4) Date: Jan. 30, 2006

(87) PCT Pub. No.: WO2005/016416
PCT Pub. Date: Feb. 24, 2005

(65) Prior Publication Data
US 2010/0268017 A1    Oct. 21, 2010

(30) Foreign Application Priority Data
Aug. 8, 2003 (DE) .................................. 103 36 902

(51) Int. Cl.
*A61M 1/10* (2006.01)
*A61M 1/12* (2006.01)
*A61M 25/00* (2006.01)

(52) U.S. Cl.
CPC .......... *A61M 1/101* (2013.01); *A61M 1/1074* (2014.02); *A61M 1/125* (2014.02); *A61M 1/1008* (2014.02); *A61M 1/122* (2014.02); *A61M 25/0041* (2013.01); *A61M 25/0069* (2013.01)

(58) Field of Classification Search
CPC ............ A61M 2001/122; A61M 1/101; A61M 1/125; A61M 25/0041; A61M 25/0069
USPC .......................................................... 600/16
See application file for complete search history.

(56) References Cited

U.S. PATENT DOCUMENTS

| | | |
|---|---|---|
| 2,350,534 A | 6/1944 | Rosinger |
| 3,333,127 A | 7/1967 | Congdon et al. |
| 3,354,833 A | 11/1967 | Laing |
| 3,489,145 A | 1/1970 | Judson et al. |
| 3,936,683 A | 2/1976 | Walker |

(Continued)

FOREIGN PATENT DOCUMENTS

| | | |
|---|---|---|
| CA | 2613175 A1 | 1/2007 |
| CA | 2632420 A1 | 6/2007 |

(Continued)

OTHER PUBLICATIONS

Brochure Impella Pumpsystem of Impella CardioSystems AG, "Turning Lives Around," Aug. 2003 (4 pages).

(Continued)

*Primary Examiner* — Catherine Voorhees
*Assistant Examiner* — Roland Dinga
(74) *Attorney, Agent, or Firm* — White & Case LLP

(57) ABSTRACT

The intracardiac pumping device has a pump (11) connected at its distal end (13) to a canula (15). At the distal end, the canula (15) has a suction head (16) for drawing blood. The suction head is extended by a non-sucking projection (20). The projection stabilizes the position of the pumping device in the heart. It extends the canula (15) mechanically without degrading the hydraulic conditions. It also serves as a spacer to prevent the suction head (16) from adhering to a wall of the heart.

8 Claims, 4 Drawing Sheets

(56) References Cited

U.S. PATENT DOCUMENTS

| | | | |
|---|---|---|---|
| 4,065,234 A | 12/1977 | Yoshiyuki et al. | |
| 4,115,040 A | 9/1978 | Knorr | |
| 4,135,253 A | 1/1979 | Reich et al. | |
| 4,153,048 A * | 5/1979 | Magrini | A61B 5/6857 600/505 |
| 4,420,851 A | 12/1983 | Wiener | |
| 4,679,558 A | 7/1987 | Kensey et al. | |
| 4,686,982 A | 8/1987 | Nash | |
| 4,728,319 A | 3/1988 | Masch | |
| 4,747,821 A | 5/1988 | Kensey et al. | |
| 4,747,840 A * | 5/1988 | Ladika | A61M 25/0041 604/264 |
| 4,749,376 A | 6/1988 | Kensey et al. | |
| 4,753,221 A | 6/1988 | Kensey et al. | |
| 4,777,951 A * | 10/1988 | Cribier | A61M 25/0023 600/485 |
| 4,846,152 A | 7/1989 | Wampler et al. | |
| 4,895,557 A | 1/1990 | Moise et al. | |
| 4,919,647 A | 4/1990 | Nash | |
| 4,984,972 A | 1/1991 | Clausen et al. | |
| 5,011,469 A | 4/1991 | Buckberg et al. | |
| 5,017,103 A | 5/1991 | Dahl | |
| 5,037,403 A * | 8/1991 | Garcia | 604/532 |
| 5,042,984 A | 8/1991 | Kensey et al. | |
| 5,061,256 A * | 10/1991 | Wampler | 604/523 |
| 5,097,849 A | 3/1992 | Kensey et al. | |
| 5,147,186 A | 9/1992 | Buckholtz | |
| 5,158,279 A | 10/1992 | Laffey et al. | |
| 5,163,431 A * | 11/1992 | Griep | 600/435 |
| 5,169,378 A | 12/1992 | Figuera | |
| 5,250,059 A | 10/1993 | Andreas et al. | |
| 5,275,580 A | 1/1994 | Yamazaki | |
| 5,357,963 A | 10/1994 | Mayol et al. | |
| 5,376,114 A | 12/1994 | Jarvik | |
| 5,405,383 A | 4/1995 | Barr | |
| 5,421,338 A | 6/1995 | Crowley et al. | |
| 5,480,392 A * | 1/1996 | Mous | 604/530 |
| 5,749,855 A | 5/1998 | Reitan | |
| 5,827,171 A | 10/1998 | Dobak, III et al. | |
| 5,863,179 A | 1/1999 | Westphal et al. | |
| 5,888,241 A | 3/1999 | Jarvik | |
| 5,921,923 A | 7/1999 | Kuck et al. | |
| 5,928,132 A | 7/1999 | Leschinsky | |
| 5,938,672 A | 8/1999 | Nash | |
| 5,954,745 A | 9/1999 | Gertler et al. | |
| 6,001,078 A | 12/1999 | Reekers | |
| 6,054,788 A | 4/2000 | Dombrovski et al. | |
| 6,083,260 A | 7/2000 | Aboul-Hosn | |
| 6,123,725 A | 9/2000 | Aboul-Hosn | |
| 6,129,704 A | 10/2000 | Forman et al. | |
| 6,183,220 B1 | 2/2001 | Ohara et al. | |
| 6,245,007 B1 | 6/2001 | Bedingham et al. | |
| 6,295,877 B1 | 10/2001 | Aboul-Hosn et al. | |
| 6,413,222 B1 | 7/2002 | Pantages et al. | |
| 6,517,528 B1 | 2/2003 | Pantages et al. | |
| 6,533,716 B1 | 3/2003 | Schmitz-Rode et al. | |
| 6,537,247 B2 | 3/2003 | Shannon | |
| 6,544,216 B1 * | 4/2003 | Sammler et al. | 604/95.03 |
| 6,841,910 B2 | 1/2005 | Gery | |
| 6,858,001 B1 | 2/2005 | Aboul-Hosn | |
| 6,974,436 B1 | 12/2005 | Aboul-Hosn et al. | |
| 6,976,996 B1 | 12/2005 | Aboul-Hosn | |
| 6,981,942 B2 | 1/2006 | Khaw et al. | |
| 7,022,100 B1 | 4/2006 | Aboul-Hosn et al. | |
| 7,027,875 B2 | 4/2006 | Siess et al. | |
| 7,393,181 B2 | 7/2008 | McBride et al. | |
| 7,646,376 B2 | 1/2010 | Blersch | |
| 7,731,675 B2 | 6/2010 | Aboul-Hosn et al. | |
| 7,841,976 B2 | 11/2010 | McBride et al. | |
| 7,927,068 B2 | 4/2011 | McBride et al. | |
| 8,439,859 B2 | 5/2013 | Pfeffer et al. | |
| 8,888,728 B2 | 11/2014 | Aboul-Hosn et al. | |
| 9,545,468 B2 | 1/2017 | Aboul-Hosn et al. | |
| 9,561,314 B2 | 2/2017 | Aboul-Hosn et al. | |
| 9,597,437 B2 | 3/2017 | Aboul-Hosn et al. | |
| 2001/0000528 A1 | 4/2001 | Cho | |
| 2002/0151799 A1 | 10/2002 | Pantages et al. | |
| 2003/0135086 A1 | 7/2003 | Khaw et al. | |
| 2003/0135940 A1 | 7/2003 | Lev et al. | |
| 2003/0208097 A1 | 11/2003 | Aboul-Hosn et al. | |
| 2004/0022640 A1 * | 2/2004 | Siess et al. | 417/53 |
| 2004/0044266 A1 * | 3/2004 | Siess et al. | 600/16 |
| 2004/0113502 A1 | 6/2004 | Li et al. | |
| 2004/0193046 A1 | 9/2004 | Nash et al. | |
| 2004/0260237 A1 | 12/2004 | Squadrito | |
| 2005/0135942 A1 | 6/2005 | Wood et al. | |
| 2006/0008349 A1 | 1/2006 | Khaw | |
| 2006/0062672 A1 | 3/2006 | McBride et al. | |
| 2006/0195004 A1 | 8/2006 | Jarvik | |
| 2007/0118072 A1 | 5/2007 | Nash | |
| 2008/0103591 A1 | 5/2008 | Siess | |
| 2008/0114339 A1 | 5/2008 | McBride et al. | |
| 2008/0132747 A1 | 6/2008 | Shifflette | |
| 2008/0183136 A1 | 7/2008 | Lenker et al. | |
| 2009/0060743 A1 | 3/2009 | McBride et al. | |
| 2009/0062597 A1 | 3/2009 | Shifflette | |
| 2009/0088609 A1 | 4/2009 | Schmitz-Rode et al. | |
| 2009/0093764 A1 | 4/2009 | Pfeffer et al. | |
| 2009/0093796 A1 | 4/2009 | Pfeffer et al. | |
| 2009/0218728 A1 | 9/2009 | Moyer | |
| 2009/0227892 A1 | 9/2009 | Krombach et al. | |
| 2010/0210895 A1 | 8/2010 | Aboul-Hosn et al. | |
| 2010/0268017 A1 | 10/2010 | Siess | |
| 2011/0071338 A1 | 3/2011 | McBride et al. | |
| 2013/0066140 A1 | 3/2013 | McBride et al. | |
| 2015/0073202 A1 | 3/2015 | Aboul-Hosn et al. | |
| 2016/0106899 A1 * | 4/2016 | Aboul-Hosn | A61M 1/101 600/16 |

FOREIGN PATENT DOCUMENTS

| | | |
|---|---|---|
| DE | 4414903 A1 | 11/1995 |
| DE | 100 59 714 C1 | 5/2002 |
| DE | 10336902 B3 | 8/2004 |
| DE | 102005039950 A1 | 3/2007 |
| EP | 0364293 A2 | 4/1990 |
| EP | 0445782 A1 | 9/1991 |
| EP | 0445782 A1 | 11/1991 |
| EP | 0768900 A1 | 4/1997 |
| EP | 0914171 A2 | 5/1999 |
| EP | 0916359 A1 | 5/1999 |
| EP | 0916359 A1 | 5/1999 |
| EP | 1034808 A1 | 9/2000 |
| EP | 1207934 A2 | 5/2002 |
| EP | 2047872 A1 | 4/2009 |
| EP | 2229965 A1 | 9/2010 |
| FR | 2788223 | 7/2000 |
| JP | H04126158 A | 4/1992 |
| WO | WO99/02204 | 1/1999 |
| WO | WO-1999044651 A1 | 9/1999 |
| WO | WO-99/58170 A1 | 11/1999 |
| WO | WO-2000019097 | 4/2000 |
| WO | WO-0043053 A1 | 7/2000 |
| WO | WO-2000043053 | 7/2000 |
| WO | WO-2000057805 | 10/2000 |
| WO | WO-01017581 | 3/2001 |
| WO | WO 01/83016 A2 | 8/2001 |
| WO | WO-2001083016 | 11/2001 |
| WO | WO-02/22200 A1 | 3/2002 |
| WO | WO/02/43791 * | 6/2002 ..... 600/16 |
| WO | WO-02/43791 A1 | 6/2002 |
| WO | WO-2003103745 | 12/2003 |
| WO | 2005016416 A1 | 2/2005 |
| WO | WO-2006020942 A1 | 2/2006 |
| WO | WO-2006034158 A2 | 3/2006 |
| WO | 2007112033 A2 | 10/2007 |
| WO | WO-2010063494 A1 | 6/2010 |

OTHER PUBLICATIONS

Buecker et al., "Use of a Nonmetallic Guide Wire for Magnetic Resonance-Guided Coronary Artery Catheterization," Investigative Radiology, 39:11, pp. 656-660 (2004).

(56) References Cited

OTHER PUBLICATIONS

Compendium of Technical and Scientific Information for the Hemopump Temporary Cardiac Assist System, 1988 (15 pages).
Dekker, Andre, et al, "Efficacy of a New Intraaortic Propeller Pump vs the Intraaortic Balloon Pump," Chest Journal; Jun. 2003 (7 pages).
Frazier, O.H., et al, "First Human Use of the Hemopump, A Cather-Mounted Ventricular Assist Device," Ann Thorac Surg., Feb. 1990; 49(2): pp. 299-304.
International Preliminary Report on Patentability, from PCT/EPOS/008858, issued Jun. 7, 2011.
JOMED Reitan Catheter Pump Brochure, www.jomed.com/rcp (undated) (6 pages).
Lueger, Lexikon der Technik, "Lexikon der Feinwerktechnik", 1968, vol. 13, Deutsche Verlags-Anstalt GmbH, Stuttgart, seite 551.
Reitan, Oyvind et al, "Hydrodynamic Properties of a New Percutaneous Intra-aortic Axial Flow Pump," ASAIO Journal; Jay-Jun. 2000; vol. 16; pp. 323-329.
Rothman, Martin T, "The Reitan Catheter Pump: A New Versatile Approach for Hemodynamic Support," London Chest Hospital Barts & The Long NHS Trust, presented at TCT Conference, Oct. 24-26, 2006, (40 pages).
Schmitz-Rode, T et al. 2005. An Expandable Percutaneous Catheter Pump for Left Ventricular Support. Journal of the American College of Cardiology, 45:11, pp. 1856-1861.
Schmitz-Rode, T et al. 2006. Temporary Pulmonary Stent Placement as Emergency Treatment of Pulmonary Embolism. Journal of the American College of Cardiology, 48:4, pp. 812-816.
Siess, Thorsten, "Systemanalyse und Entwicklung intravasaler Rotationspumpen zur Herzunterstutzung," Helmholtz-Institut, Jun. 24, 1998 (105 pages) and partial English translation (37 pages).
Verma, R et al. 2006. Evaluation of a Newly Developed Percutaneous Thrombectomy Basket Device m Sheep with Central Pulmonary Embolisms. Investigative Radiology, 41:10, pp. 729-734.
Wampler, Richard, K., "In Vivo Evaluation of a Peripheral Vascular Access Axial Flow Blood Pump," ASAIO Trans., Jul.-Sep. 1988;34(3): pp. 450-454.
U.S. Appl. No. 09/280,988 (24 pages).
Judgement in German Nullity Proceedings of related application DE10336902, FPC Judgment with Pictures, English translation; Senior Registrar as clerk of the court; Pronounced on Nov. 15, 2016; pp. 1-38.
Morton J. Kern, The Cardiac Catheterization Handbook, 4th Edition, 2003, Mosby Inc., pp. 114-116, 144, 267, 281-282 and 636.
Cordis Decor Catheters and the Angiographic System, Cordis Corporation, 1982, (17 pages).
Exhibit in German Nullity Proceedings of related Application DE10336902—Exhibit HL 19; image from U.S. Pat. No. 5,061,256; Oct. 12, 2014; (1 page).
Exhibit in German Nullity Proceedings of related application DE10336902—Exhibit HL20; image from U.S. Pat. No. 6,533,716; Oct. 12, 2014; (1 page).
Exhibit in German Nullity Proceedings of related application DE10336902—Exhibit HL21; Oct. 12, 2014; (1 page).
Exhibit in German Nullity Proceedings of related application DE10336902—Exhibit HL22; Oct. 8, 2015; (1 page).
Exhibit in German Nullity Proceedings of related application DE10336902—Exhibit HL23; (1 page).
Exhibit in German Nullity Proceedings of related application DE10336902—Exhibit HL25; Oct. 8, 2015; (1 page).
Exhibit in German Nullity Proceedings of related application DE10336902—Exhibit HL 31; Imager Angiographic Catheters; Medi-tech Boston Scientific Corporation; Aug. 10, 2015; (4 pages).
Exhibit in German Nullity Proceedings of related Application DE10336902—Exhibit HL 30; Diagnostic Catheters; Mallinckrodt; Aug. 10, 2015 (1 page).
Julius H. Grollman, Jr.; Editorial: Pigtail Catheters in Pulmonary Angiography; Catherization and Cardiovascular Diagnosis 10:389-391 (1984); (3 pages).
Exhibit in German Nullity Proceedings of related application DE10336902—Exhibit HL 47; Donald S. Baim and William Grossman; Grossman's Cardiac Catherization, Angiography and Intervention; 6th Edition; Lippincott Williams & Wilkins; pp. 84-87 and 257-259; Sep. 15, 2015.
Exhibit in German Nullity Proceedings of related application DE10336902—Exhibit HL 29; Teresa G. Norris; Principles of Cardiac Catheterization; Radiologic Technology 72.2 (Nov. 2000); Aug. 10, 2015 (34 pages).
Exhibit in German Nullity Proceedings of related application DE10336902—Exhibit HL 48; T. Schmitz-Rode et al.; Axial Flow Catheter Pump for Circulatory Support; Medizintechnik in der Kardiologie; pp. 142-143; Nov. 7, 2016.
Exhibit in German Nullity Proceedings of related application DE10336902—Exhibit 42; USCI Positrol II & Nycore Cardiovascular Catheters; Aug. 8, 2016; (23 pages).
PCT EP 2004 008321 IPRP for PCT/EP2004/008321 filed Jul. 24, 2004.
R.W. Smalling, "The Use of Mechanical Assist Devices in the Management of Cardiogenic Shock," Texas Heart Institute Journal, vol. 18, No. 4, 1991, pp. 275-281.
*Abiomed, Inc. et al., v. Maquet Cardiovascular, LLC*, IPR2017-01207, Petition (Paper 2), 121 pages, (PTAB Apr. 18, 2017).
Jegaden, O., "Clinical Results of Hemopump support in surgical cases," *Hôpital Vasculaire Louis Pradel*, Lyon, France, pp. 61-65, 1991.
Maquet 728/100/068 Claim Chart (192 pages), dated Dec. 15, 2015.
Maquet 468 Claim Chart (20 pages), dated Jan. 25, 2017.
Wampler et al., "Clinical Experience with the Hemopump Left Ventricular Assit Device," *Supported Complex and High Risk Coronary Angioplasty*, Springer 1st ed., Ch. 14, pp. 231-249 (1991).
U.S. Pat. No. 9,561,314 File History (819 pages).
U.S. Pat. No. 9,597,437 File History (1180 pages).
U.S. Pat. No. 9,545,468 File History (1241 pages).

\* cited by examiner

INTRACARDIAC PUMPING DEVICE

The invention relates to an intracardiac pumping device adapted to be fully inserted into the heart via adjoining vessels to assist the natural cardiac pump function or to replace the same by a continuous pumping operation.

Intracardiac blood pumps inserted percutaneously into a patient's body are highly miniaturized. They comprise a cylindrical drive portion and a cylindrical pump portion. The intake end of the pump portion is provided with a flexible canula having a suction head with lateral inlet openings at the distal end. Such a pumping device is described in EP 0 916 359 A1 (Impella). Another pumping device conveying in the distal direction is described in WO 99/58170 (Impella). In this pumping device, the pumping portion is prolonged by a flexible canula adapted to be passed through a cardiac valve. A catheter projects from the distal end of the canula, at which catheter a balloon is provided which is to be entrained by the blood flow in the body when the pumping device is inserted.

A pumping device that takes in blood through a canula and then feeds it proximally can be placed such that it leads through the aortic valve, the suction head at the end of the canula being situated in the left ventricle, while the pump outlet lies in the aorta. The operation of the continually feeding pump is superposed on the pulsating activity of the heart so that the pump is subjected to heavily pulsating pressure variations. In this context it may happen that the pump, together with the associated proximal catheter is subjected to substantial changes in position. During a systole, the catheter is pressed against the outer side of the aortic arch, whereas it is pressed against the inner side thereof during a diastole. Further, the position of the pump varies continuously, which may result in displacements of the canula passing through the aortic valve and even in an ejection of the canula which then slips from the cardiac valve into the aorta.

It is another difficulty with such blood pumps that the suction head may adhere to tissue parts inside the heart by suction. This entails the danger of irritations of the heart and, further, the pumping capacity is reduced by the obstruction of inlet openings. Finally, it may happen that the canula adheres to the mitral valve by suction and an additional damage to the blood is induced by suction.

It is an object of the present invention to provide an intracardiac pumping device for percutaneous insertion that substantially avoids the risk of adhering by suction.

The present pumping device has the features of claim 1. According thereto, a flexible projection is provided at the canula distal of the inlet openings. The projection forms a mechanical spacer maintaining a distance to neighboring walls, yet does not change the pumping device hydraulically.

Beside the spacing function, the projection has other effects. It increases the mechanical length of the pumping device without increasing the hydraulic length. The increase in mechanical length has the consequence that the pumping device is less likely to slip out through the aortic valve. On the other hand, the hydraulic resistance of the canula is not increased so that the suction performance is not degraded. It is another effect that the projection essentially reduces the tendency of the pumping device to make pulsating motions caused by cardiac pulsation. The pumping device including the pump and the catheter lies much calmer within the heart, whereby also the danger of an ejection is reduced. In the event that a new insertion is to be allowed after an ejection, the distal projection is preferably configured such that a new retrograde passage of the aortic valve is possible easily and reproducibly.

In a preferred embodiment of the invention, the flexible projection is a hollow tube whose lumen is in communication with that of the canula. Such a pumping device is suited for use with a guide wire. When inserting the pumping device, the guide wire may be included as a stiffening means. It is also possible to first place the guide wire and to then slip the pumping device over the same. Eventually, an angled tip of the guide wire may also be pushed out from the projection to serve as a pathfinder through the vascular system. Although the lumen of the projection is in communication with the lumen of the canula, the pump does not suck through the projection. This is because the inlet openings at the suction head have a much larger cross section than the lumen of the projection so that due to the lower flow resistance the suction is affected for the much greater part through the inlet openings. A certain suction effect caused by the lumen of the projection is so small that it is negligible and is not sufficient to cause adherence by suction to other parts. Thus, other than the suction head, the projection is unable to adhere by suction. However, should the lumen of the projection be obstructed for some reason, this has no effects on the hydraulic function of the pump.

The flexible projection may comprise a pigtail tip as known from catheters and stents. The rounded pigtail tip allows for an atraumatical supporting at heart or vessel walls. Moreover, the tip is so soft and flexible that it adapts to any cavity topology by deforming. The pigtail tip also facilitates the insertion and the placing of the pumping device. Specifically, it can be used in combination with a guide wire, the pigtail tip being stretched by the guide wire during insertion. When the pigtail tip is advanced without the guide wire, a simple and reproducible retrograde passage through the aortic valve is still possible. This is of particular importance since the guide wire is removed for the pump to operate and can not be advanced again without having to remove the pump for that purpose. Should the pump be ejected from the left heart due to the systolic cardiac functions, it may be repositioned even without the wire because of the configuration of the flexible projection as a pigtail.

The following is a detailed description of embodiments of the invention with reference to the drawing. The features mentioned in the context of the embodiments do not limit the scope of the invention. The same is defined by the claims.

IN THE FIGURES

FIG. 4 illustrates an embodiment in which the suction head has a flow-shaping inflow funnel.

Figure 1:
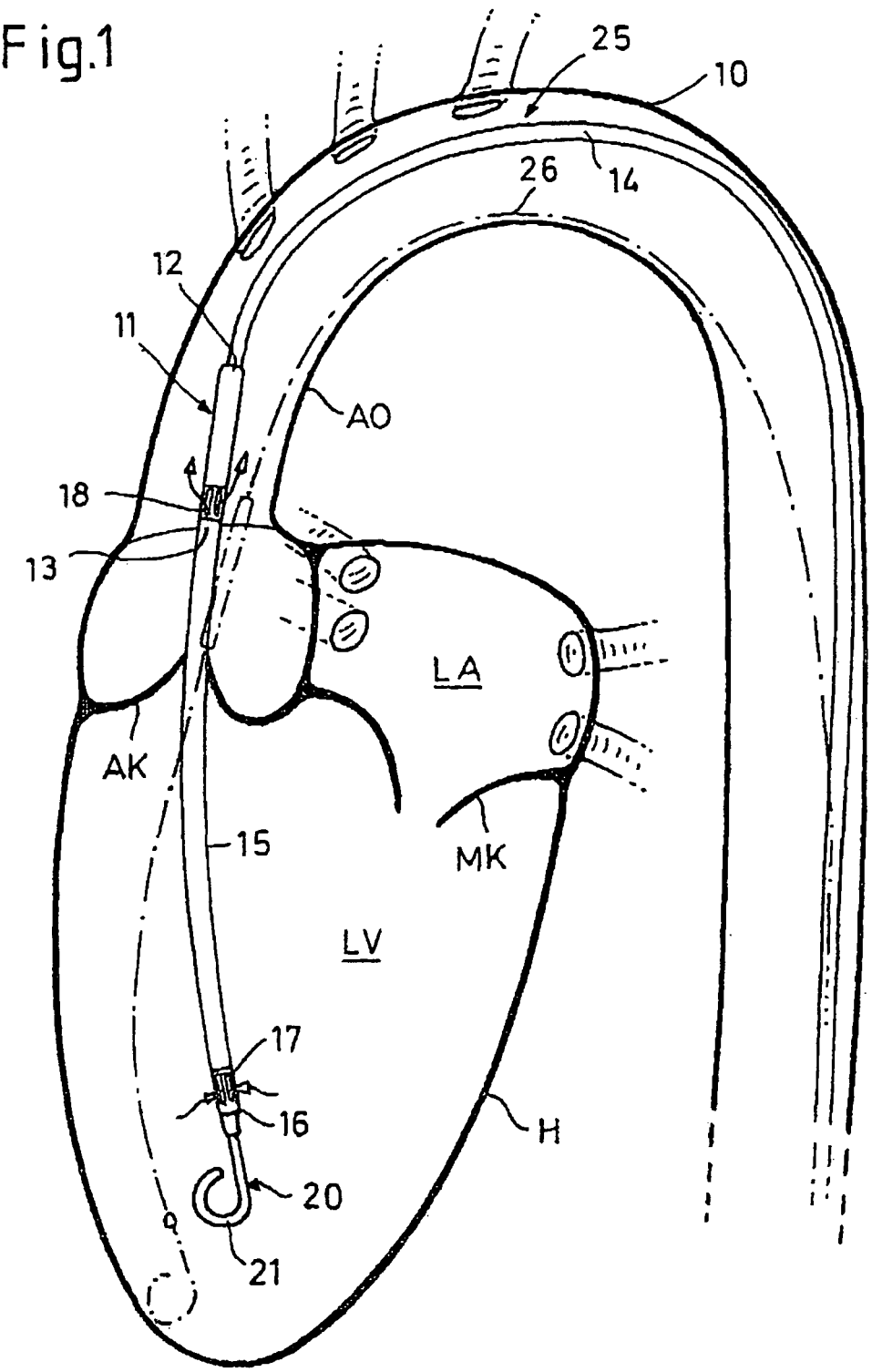
FIG. 1 illustrates the pumping device operating in the heart.

FIG. 1 illustrates the heart H with the aorta AO branching therefrom. Via the aortic arch 10, the aorta passes into a vertical strand that branches into the femoral artery, among others. The pumping device is percutaneously inserted into the femoral artery in the region of the groin and is advanced to the heart.

The intracardiac pumping device comprises a pump 11 with a proximal end 12 and a distal end 13. The pump 11 has a housing with an outer diameter of 4 mm at most and a length of approximately 15 mm so that the pump can be inserted percutaneously and be operated inside the heart. Larger pumps that can only be inserted surgically must not exceed an outer diameter of 6 mm because of the peripheral vessel diameters.

The proximal end 12 of the pump 11 is connected with a catheter 14 including the electric wires for the operation and the control of the pump 11. The distal end 13 is connected with a canula 15 which is an elongate flexible hose forming at its distal end a suction head 16 with lateral inlet openings 17. The pump 11 draws blood through the inlet openings 17 of the canula 15 and pumps the same through the outlet openings 18 provided in the sides of the pump. The pump and the canula are generally designed as described in EP 0 916 369 A1 (Impella). The canula 15 is a hose with a length of about 40 to 70 mm, whose wall is formed by a coiled wire provided with a polyurethane coating. The canula 15 has a certain form stability, yet it is flexible.

According to the invention, the suction head 16 of the canula 15 is adjoined by a projection 20 that extends the canula 15 mechanically, but not hydraulically. The projection 20 has a length of 10 to 30 mm. In the present case, it is provided with a pigtail tip 21 to allow for atraumatic support at body tissue.

The solid lines in FIG. 1 represent the extension of the pumping device in the heart H and the aorta AO. The pumping device is placed such that the pump 11 is located in the aorta AO while the suction head 16 lies in the left ventricle LV. The canula 15 extends through the aortic valve AK. Thus, the pump draws blood from the left ventricle LV and feeds into the aorta AO. Moreover, FIG. 1 shows the left atrium LA and the mitral valve MK.

The pump 11 pumps continuously at a delivery rate of 2 to 3 l/min. The reaction force tends to pull the pump into the heart. This force is countered by the pumping force of the heart. During the systole, the heart has a fluctuating delivery rate of about 10 l/min. It has been found that the pump moves resulting in a systolic position 25 at the outer side of the aortic arch 10 during the ejection phase of the heart, while, during the filling phase, a diastolic position 26 on the inner side of the aortic arch 10 is obtained. With these movements, the position of the canula 15 and the suction head 16 also changes. When the suction head 16 comes close to the trabecula structures situated at the wall of the heart, there is a danger of these structures being caught by suction, of an occlusion of the suction head, of an increased damage to the blood and the risk of a hematoma being formed in the cardiac structure.

Adhering by suction is made more difficult by the projection 20 that is supported at the wall of the heart. Further, the projection 20 forms a mechanical extension of the canula to prevent ejection from the left ventricle and the aortic valve.

Figure 2:
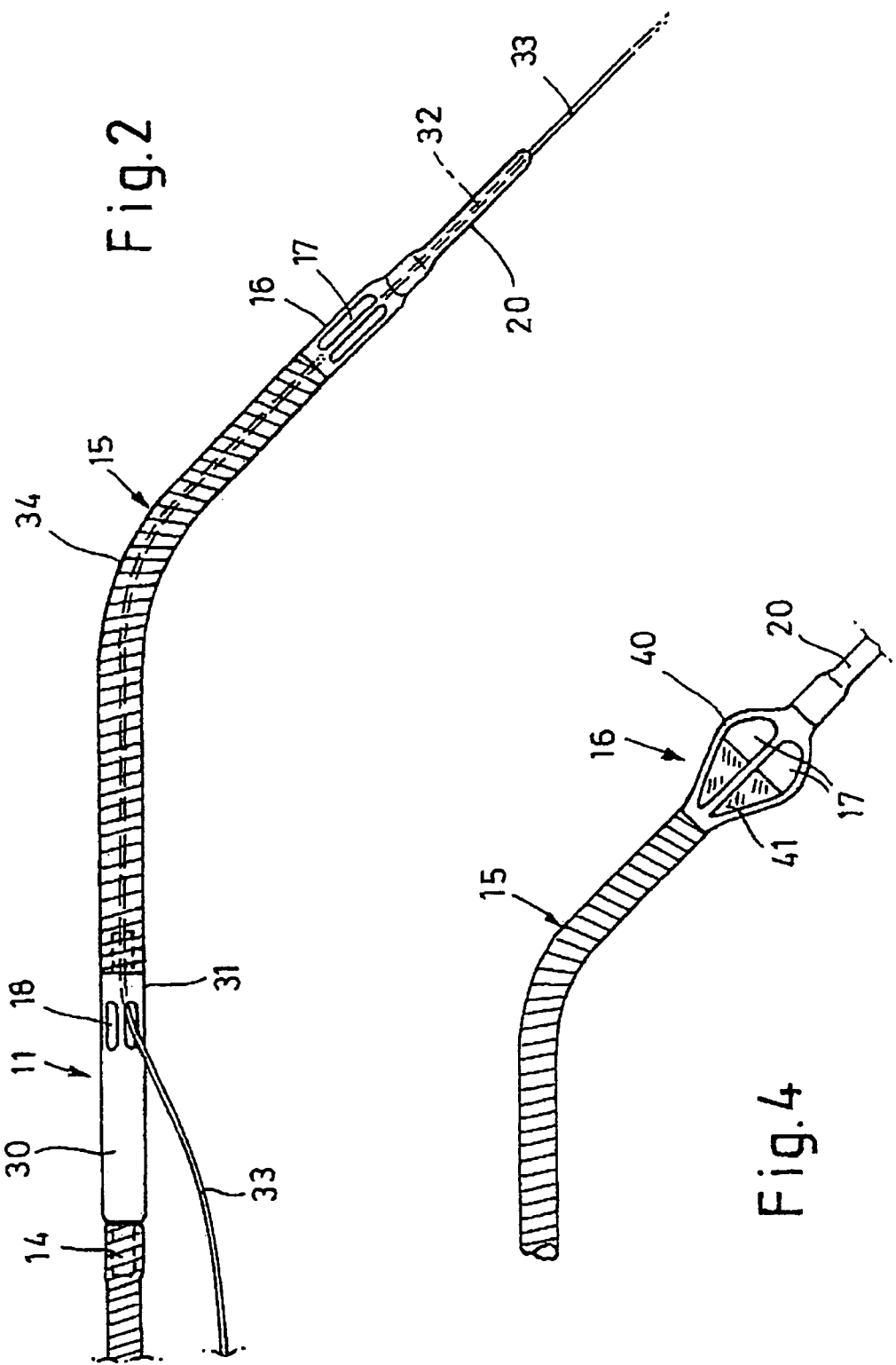
FIG. 2 illustrates the pumping device in an unused state.

As is evident from FIG. 2, the pump 11 comprises a motor part 30 and a pump part 31 arranged axially one behind the other. The pump part 31 includes a housing ring and an impeller driven by the motor and feeding the blood flow in the axial direction, the blood flow being deflected outward radially and exiting laterally from the housing of the pump 11 through the outlet openings 18. The pump part 31 is axially adjoined by the canula 15 having about the same outer diameter (4 mm) as the pump 11. The suction head 16 with the inlet opening 17 has a length of about 10 to 15 mm. The outlet openings 18 have an area at least as large as the cross-section area of the canula lumen so that the suction head forms no constriction.

In FIG. 2, the projection 20 is designed as a hollow hose with a continuous lumen 32. The width of this lumen is much smaller than that of the canula lumen. The lumen 32 serves to pass a guide wire 33 therethrough to facilitate the insertion of the pumping device into the body. The guide wire 33 extends the projection 20 if the same has a preformed bend. The guide wire may also have a soft flexible bent tip protruding from the distal end of the projection 20 and serving as a pathfinder through the vascular system. The guide wire 33 leads into the pump 11, through the pump part 31 and out from an outlet opening 18. It is then guided along the outside of the catheter 14. After the pumping device has been placed, the guide wire is withdrawn.

As illustrated in FIG. 2, the canula 15 has a preformed bend 34 that also serves to better find the path.

Figure 3:
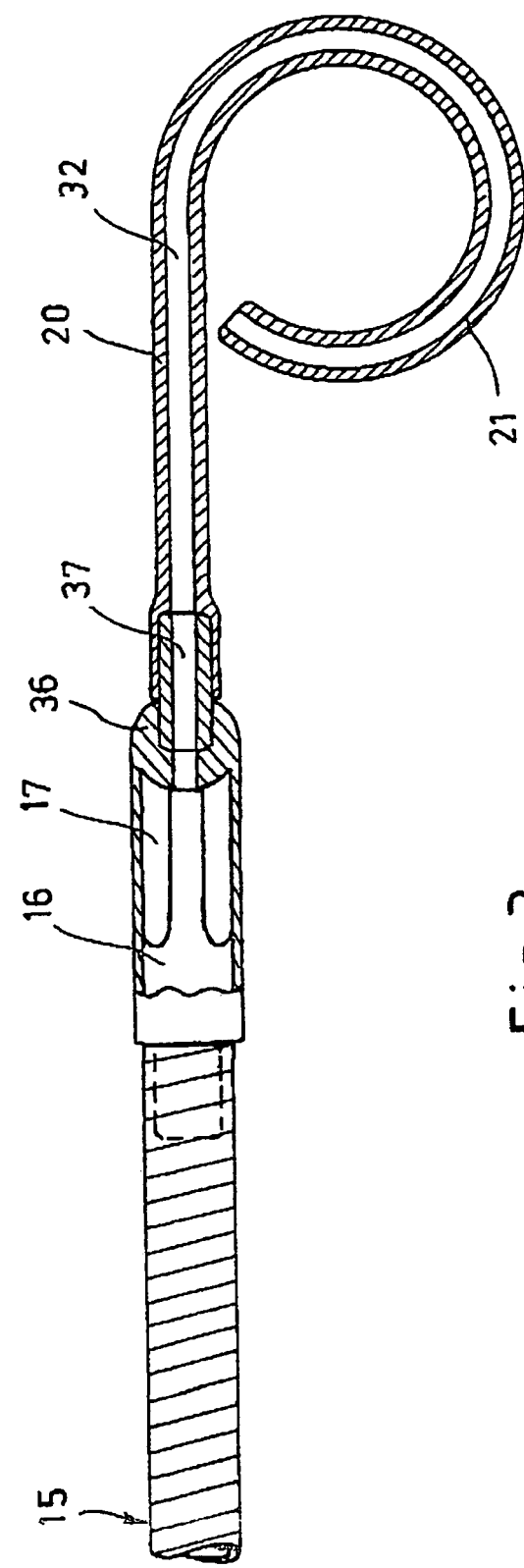
FIG. 3 shows a section through the suction head with the projection attached thereto.

FIG. 3 illustrates the distal end of the canula 15 with the suction head 16. The suction head 16 comprises the longitudinal inlet openings 17. At its end, a ball 36 is provided into which a hollow pin 37 is inserted and welded. This pin 37 serves as a connecting element for the projection 20, which in the present case is provided with a pigtail tip 21. The lumen 32 of the projection 20 extends through the pin 37 and the ball 36 into the suction head 16. Here, the outer diameter of the projection 20 is smaller than that of the canula 15.

FIG. 4 illustrates an embodiment in which the suction head 16 includes an inflow funnel 41 in an expansible suction basket 40. The suction basket 40 is made from a material able to restore itself, for example, or it is expanded by a balloon. In the expanded state, the suction basket 40 has an outer diameter larger than that of the canula 15. Thus, the suction basket 40 is expanded from its initial 4 mm to a diameter of about 6 mm. Here, the inflow funnel 41 is spanned from a flexible polymer screen that allows for a smooth inflow and substantially increases the hydraulic capacity of the pump by reducing the hydraulic losses.

Figure 5:
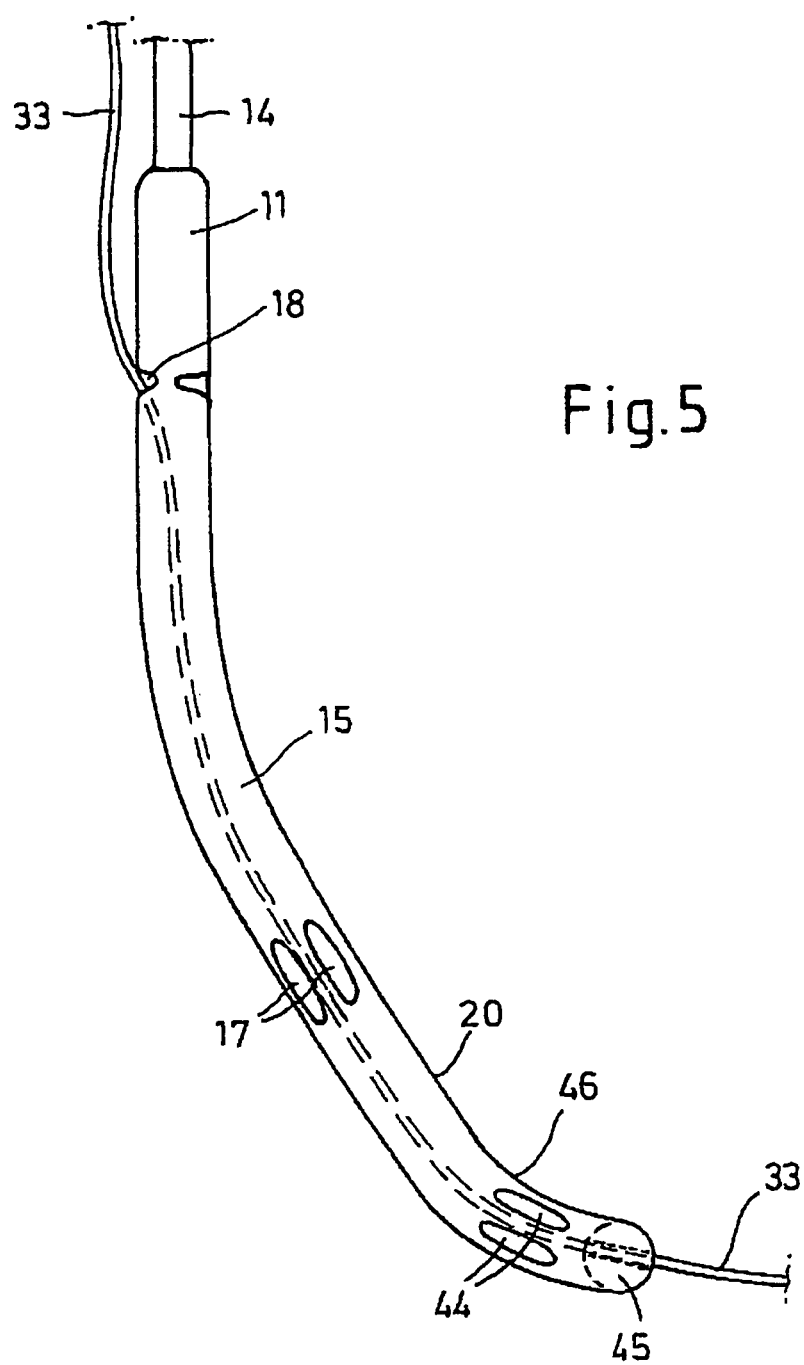
FIG. 5 illustrates an embodiment in which the canula comprises a second set of inlet openings at the end of the projection.

In the embodiment of FIG. 5, the canula 15 has a two-stage design. It is provided with first inlet openings 17 forming the main inlet. Distal of the inlet openings 17, the projection 20 follows that, in the present case, has the same outer diameter and the same lumen diameter as the canula 15. In the distal end portion of the projection 20, further lateral auxiliary openings 44 are provided that serve as auxiliary openings. No suction head is provided here. The distal end of the canula is closed by a rounded end wall 45 with a passage for a guide wire 33.

The pumping device of FIG. 5 is slipped over the guide wire 33 that passes through the impeller part 33 of the pump 11 and exits laterally from an outlet opening 18. After the pumping device has been positioned, the guide wire 33 is withdrawn in the proximal direction. The operation of the pump 11 causes blood to be drawn through the inlet openings 17. Due to the higher flow resistance of the projection 20 and the auxiliary openings 44, only the inlet openings 17 exert a suction effect, while the projection 20 has practically no hydraulic effect. Only when the inlet openings 17 adhere by suction or are clogged in another way, will the auxiliary openings 44 become effective. The projection 20 has an angled part 46. Its lumen is in communication with that of the canula 15. The projection has a flexibility that is preferably higher than that of the canula 15.

The invention claimed is:

1. An intracardiac pumping device for percutaneous insertion, comprising a pump connected at the proximal end with a catheter and at the suction-side distal end with a canula having inlet openings remote from the pump, characterized in that a flexible pigtail tip is provided at the canula distal of all of the inlet openings, wherein said flexible pigtail tip forms a spacer for keeping said inlet openings spaced apart from adjacent heart walls.

2. The pumping device of claim 1, wherein the pigtail tip comprises a non-sucking projection.

3. The pumping device of claim 1, wherein the pigtail tip comprises a hollow hose whose lumen is in communication with that of the canula.

4. The pumping device of claim 1, wherein the inlet openings are provided in an expansible suction basket including an inflow funnel.

5. The pumping device of claim 1, wherein the pigtail tip has an outer diameter that is smaller than that of the canula.

6. The pumping device of claim 1, wherein the canula has a preformed bend.

7. The pumping device of claim 1, wherein a guide wire is provided that leads through the pump and is adapted to be advanced from the canula into the pigtail tip.

8. The pumping device of claim 1, wherein the pigtail tip has lateral auxiliary openings.

* * * * *